United States Patent [19]

Damon

[11] Patent Number: 4,845,422

[45] Date of Patent: Jul. 4, 1989

[54] MICROWAVE PROXIMITY SENSOR

[75] Inventor: Edward K. Damon, Columbus, Ohio

[73] Assignee: General Electric Company, Cincinnati, Ohio

[21] Appl. No.: 946,357

[22] Filed: Dec. 24, 1986

[51] Int. Cl.⁴ .............................................. G01N 22/00
[52] U.S. Cl. .......................... 324/585 R; 324/58.5 C; 333/159; 333/161; 340/552; 361/179
[58] Field of Search ................ 324/58 C, 58 A, 58 B, 324/58 R, 58.5 A, 58.5 B, 58.5 R, 58.5 C; 361/179, 180; 356/356, 358; 340/551, 552, 553, 561, 562; 333/161, 159, 246, 248, 156

[56] References Cited

U.S. PATENT DOCUMENTS

| | | | |
|---|---|---|---|
| 3,181,091 | 4/1965 | Augustine et al. | 333/159 |
| 3,656,179 | 4/1972 | DeLoach | 333/161 |
| 3,757,330 | 9/1973 | Hotston | 343/12 R |
| 4,123,702 | 10/1978 | Kinanen et al. | 324/58.5 A |
| 4,123,703 | 10/1978 | Robinson | 324/58.5 B |
| 4,398,161 | 8/1983 | Lamb et al. | 333/156 |
| 4,520,308 | 5/1985 | Rohde et al. | 324/58.5 R |
| 4,538,124 | 8/1985 | Morrison | 333/246 |
| 4,581,595 | 4/1986 | Silagi | 333/156 X |

*Primary Examiner*—Reinhard J. Eisenzopf
*Assistant Examiner*—Robert W. Mueller
*Attorney, Agent, or Firm*—Derek P. Lawrence; Nathan D. Herkamp

[57] ABSTRACT

The invention relates to a type of proximity sensor. In one form, two sinusoidal signals travel along two transmission lines near an object. When the distance between one or both of the lines and the object changes, the speed of travel of one or both of the signals changes. There is a correlation between the speed change and the distance, thus allowing one to infer distance from speed change. One way to measure the speed change is to measure the phase relationship between the two signals.

3 Claims, 5 Drawing Sheets

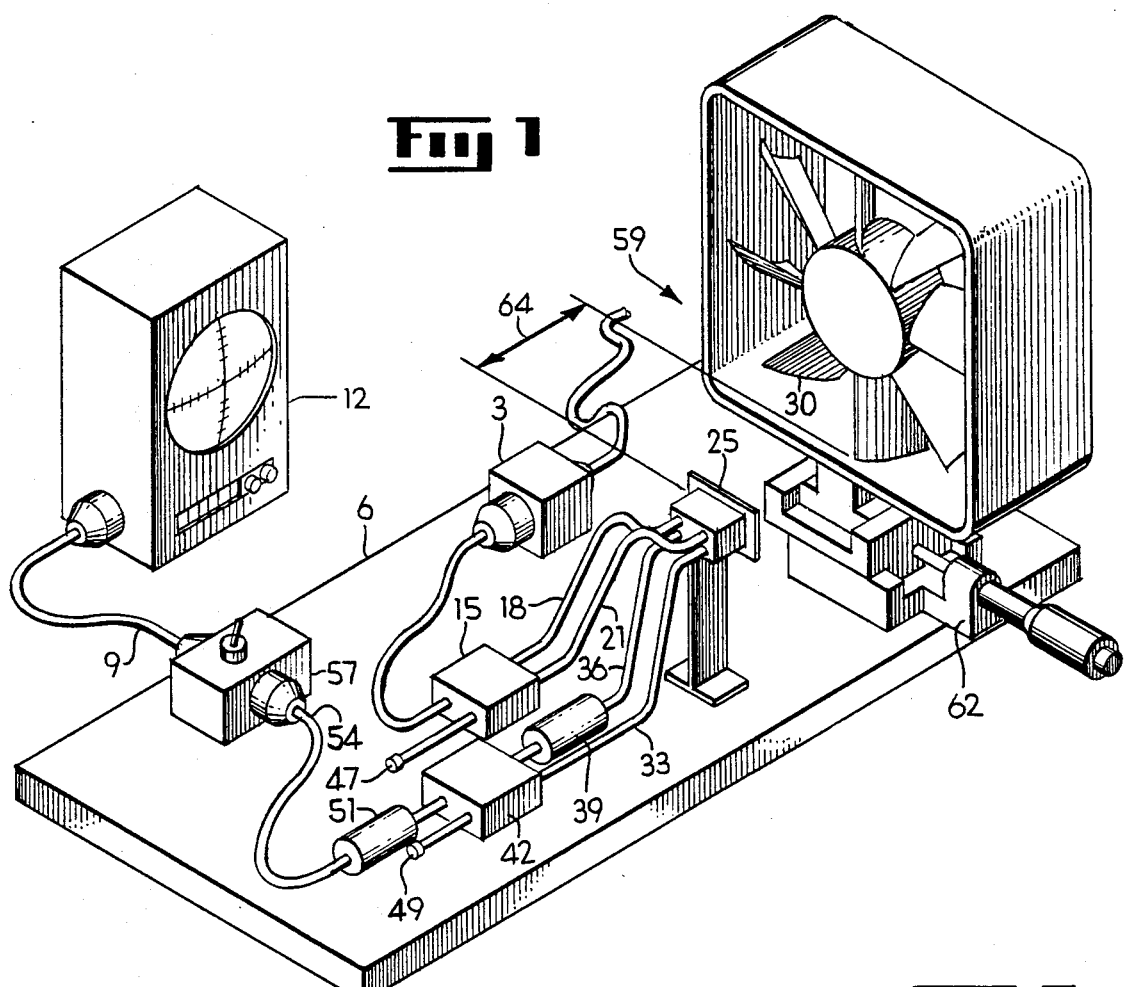
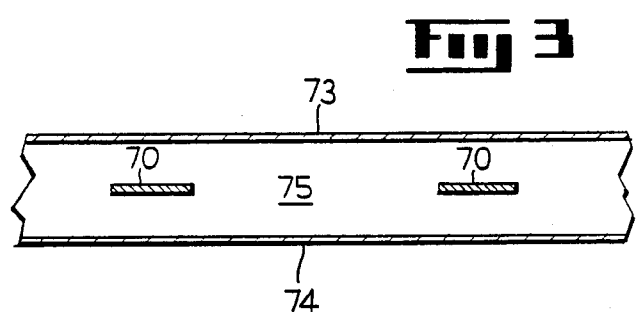
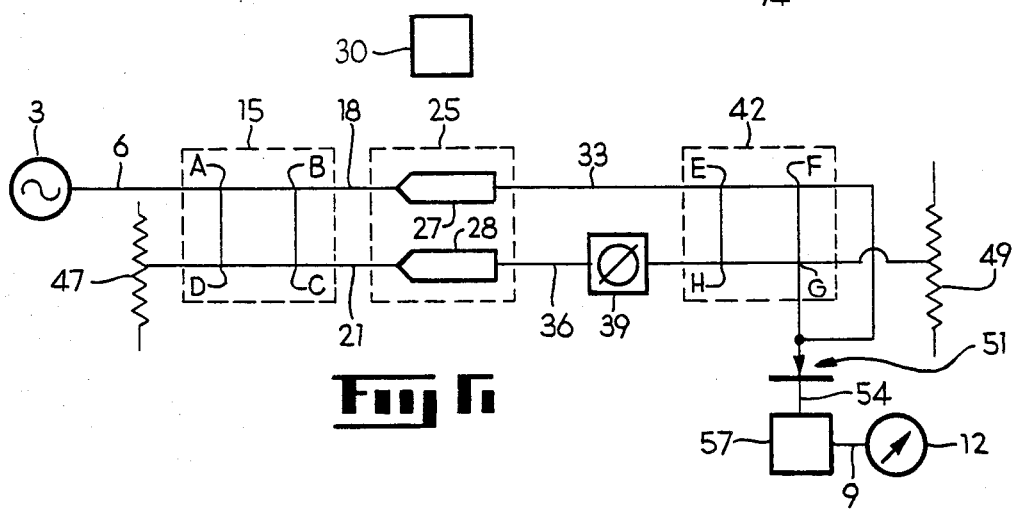

MICROWAVE PROXIMITY SENSOR

The invention relates the measurement of distances, using microwave radiation.

BACKGROUND OF THE INVENTION

There exist numerous techniques for noncontact measurement of small distances on the order of one inch to small fractions of an inch. These techniques may use capacitive, magnetic, optical, or acoustic effects, with each technique having particular advantages in a given situation. The choice of technique frequently depends upon the required accuracy, the operating medium, and upon environmental constraints.

OBJECTS OF THE INVENTION

It is an object of the present invention to provide a new and improved distance sensor.

SUMMARY OF THE INVENTION

In one form of the invention, two sinusoidal electromagnetic signals are transmitted along separate transmission lines. When an object is near one of the lines, the speed of travel of the signal on that line is changed. The amount of change is a function (generally nonlinear) of the distance between the object and the transmission line. Measurement of the change allows one to infer the distance. The change in speed of travel is determined through a phase shift of the sinusoidal electromagnetic signal. Further, phase changes may also be used to infer changes in the object geometry or in the surrounding medium.

BRIEF DESCRIPTION OF THE DRAWINGS

FIG. 1 illustrates one form of the present invention.

FIG. 3 is a cross-sectional view of a form of transmission line generally called a stripline. (Two parallel striplines are shown).

FIG. 9 is typical of a set of calibration curves when lateral motion is allowed.

DETAILED DESCRIPTION OF THE INVENTION

Figure 6:
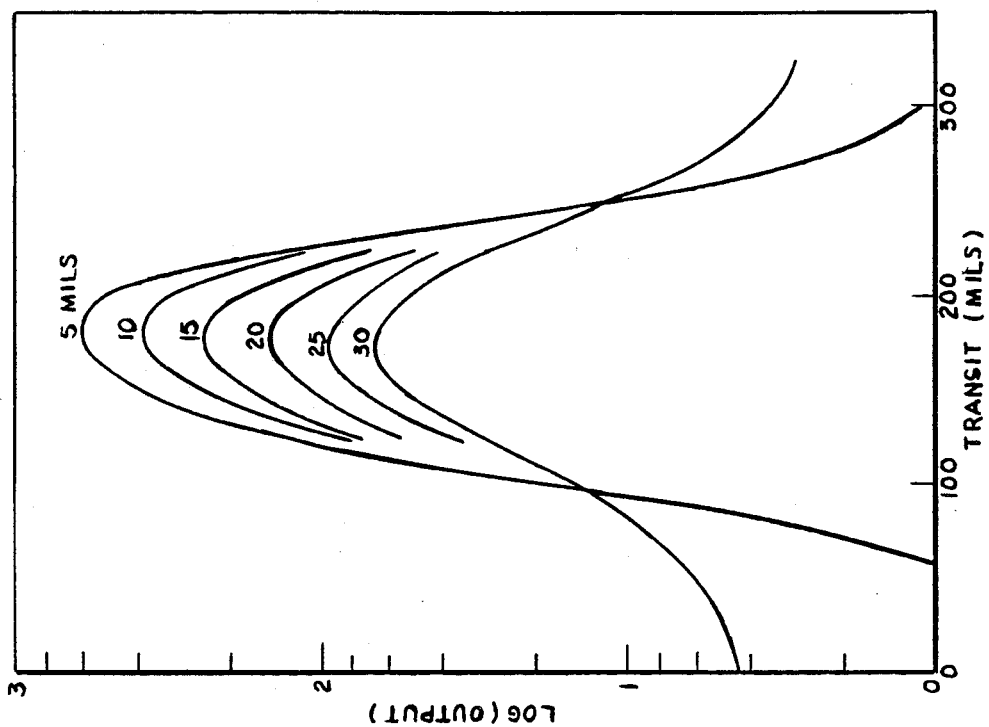
FIG. 6 is a schematic of the microwave circuitry of in FIG. 1 or FIG. 5.

FIGS. 1 and 6 will be considered together. A listing of typical relevant components is given in Table 1, together with suppliers from which they can be obtained. The electromagnetic source 3 is a Gunn diode oscillator operating at 10.5 gigahertz (GHz) which provides an input signal on line 6. All connections in FIG. 1 are coaxial lines suitable for the frequencies employed. The signal splitter 15 is a microwave hybrid

TABLE 1

3—ESC Model 206 dielectric resonator stabilized oscillator or M/A-COM Gunn MA86651A
15 and 42—OmniSpectra 2032-6348-00 Hybrid Coupler
39—OmniSpectra 2054-60002-00 line stretcher
51—OmniSpectra 2085-6017-00 detector
62—Line Tool Co. Model I-1 Micropositioner
47 and 49—Midisco MDC 1075 precision terminations
Microwave connectors are OSM or SMA types.

circuit which splits the input signal into two signals carried by lines 18 and 21, the two signals being 90° out of phase and of approximately equal amplitudes in this implementation. Termination 47 absorbs incidental unwanted reflected signal.

The two signals are fed to the sensor 25 which contains elements 27 and 28 which will be called sensing lines. At the present time, it is sufficient to state that when an object, such as a fan blade in FIG. 1, is near one of the sensing lines, 27 for example, the propagation of the signal along that sensing line is changed.

The two signals, after passing along the sensing lines, exit the sensor 25 on lines 33 and 36 shown in both Figures. The signals are recombined in signal splitter 42, which is identical to splitter 15. The phase shifter 39 is adjusted so that the phasor addition of the two signals results in an addition at port G and cancellation, or a null, at port F. This compensates for unequl path lengths in 18, 21, 25, 33, 36, as well as imperfections in the splitters and elsewhere. The unwanted power at port G is absorbed in termination 49 or used to monitor the operation of the source 3. The null signal at port F is the useful signal output. In this implementation, it is rectified by video detector 51, amplified by amplifier 57, and displayed by meter or oscilloscope 12. Distance measurement using port F will now be described.

In the absence of any object near the sensing lines, phase shifter 39 is first adjusted for a null, ideally zero, signal at port F. Then, any object approaching one of the sensing lines will then create a phase change in the signal on that line such that the signal level at port F will change. This resulting signal can be calibrated in terms of distance for a given object.

Figure 7:
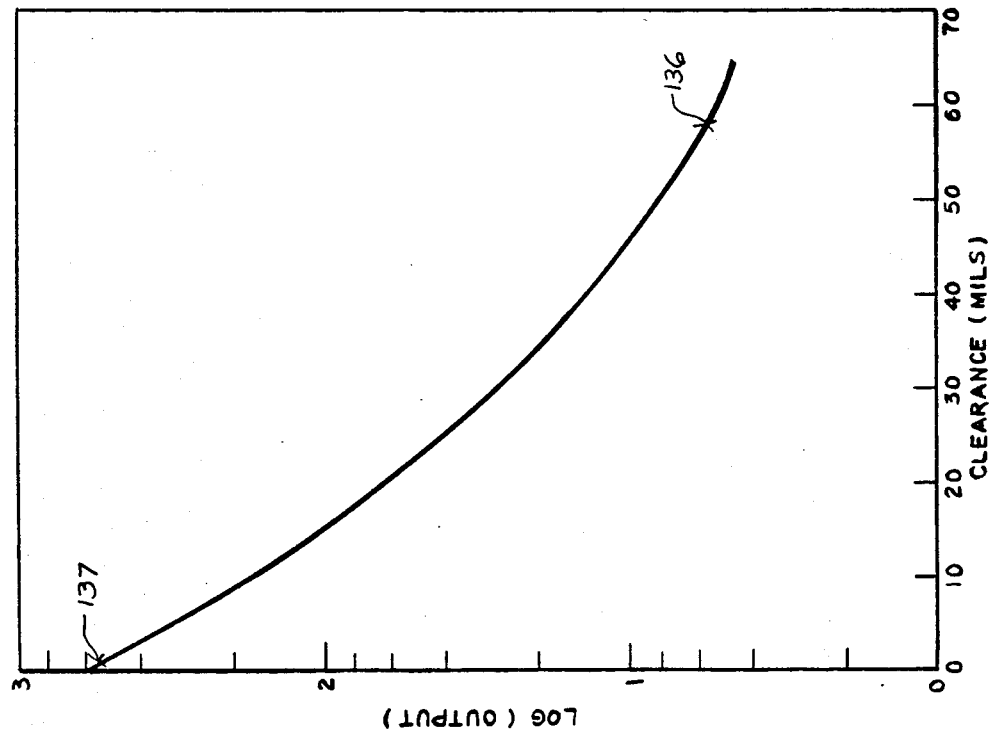
FIG. 7 is a typical calibration curve.

The Inventor has performed an experiment using the apparatus shown in FIG. 1 and has obtained the data shown in FIG. 7 and FIG. 9. In the experiment, a stationary object, which can be fan blade 30 when the fan is not spinning, was moved toward and away from sensor 25 by cross-slide table 62. Distance 64 is represented by the horizontal axis in FIG. 7. The Inventor points out one significant feature of FIG. 7, which is that the vertical axis is on a logarithmic scale. For example, point 137 represents a voltage which is a hundred times greater than that at point 136. The apparatus shown in FIG. 1 has thus been found useful in measuring distances, such as distance 64.

A more detailed description of sensor 25 will now be given. FIG. 3 illustrates in cross section a typical stripline, although other forms of transmission lines such as those generally known as microstrip or slotline, for example, should also be useful. Independent striplines 70 are sandwiched between conducting ground planes 73 and 74 and separated from the ground planes by a dielectric material. The dielectric ground planes may be air or any suitable insulator known in the art. A typical separation of the ground planes may be 0.050 inch, and the width of the stripline 70 may be approximately one-tenth this spacing, although wider excursions are sometimes used.

Figure 4:
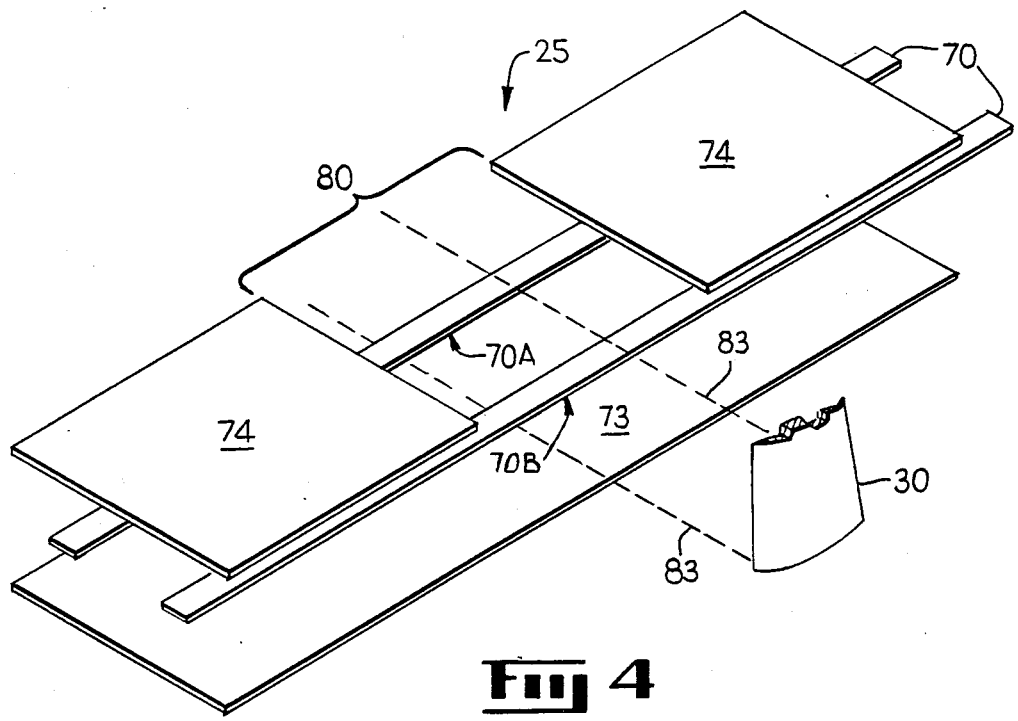
FIG. 4 is another form of the sensor shown in FIG. 2.

FIG. 4 is an exploded view of a stripline of the type in FIG. 3. A section 80 of one of the ground planes 74 has been eliminated. The exposed striplines 70A and 70B correspond to sensing lines 27 and 28 shown in FIG. 6. Consequently, when an object 30 is near one of the striplines, the speed of propagation of the signal is changed in that line, as mentioned above.

Figure 2:
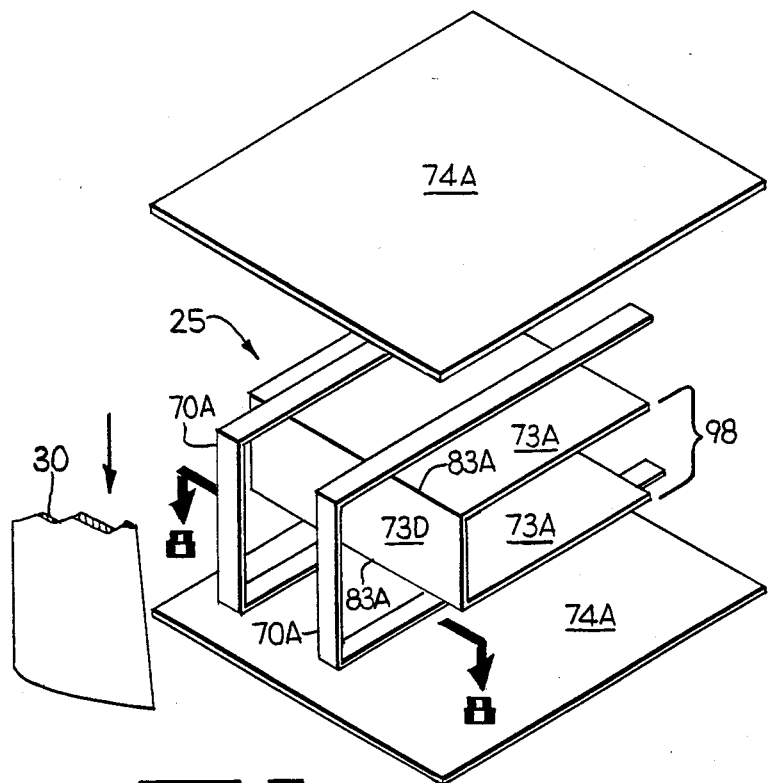
FIG. 2 is an exploded view of the sensor 25 in FIG. 1.

FIG. 2 shows an alternate form of the invention shown in FIG. 4. In a broad sense, the stripline of FIG. 4 is folded along dashed lines 83 which correspond to edges 83A in FIG. 2. Stripline regions 70A and 70B correspond to the sensing line 27 and 28 shown in FIG. 6. Folded ground plane 73A corresponds to the flat continuous ground plane 73 in FIG. 4, while the two ground planes 74A in FIG. 2 correspond to the discontinuous ground plane 74 in FIG. 4. Again, when an object 30 is near stripline section 70A, propagation in the stripline is altered. It is, of course, recognized that FIGS. 2 and 4 show only the conductive elements of the sensor 25, with the dielectric not shown. In addition, minor changes in geometry known in the art affecting impedance in order to compensate for the bending and ground plane changes are not shown.

Figure 5:
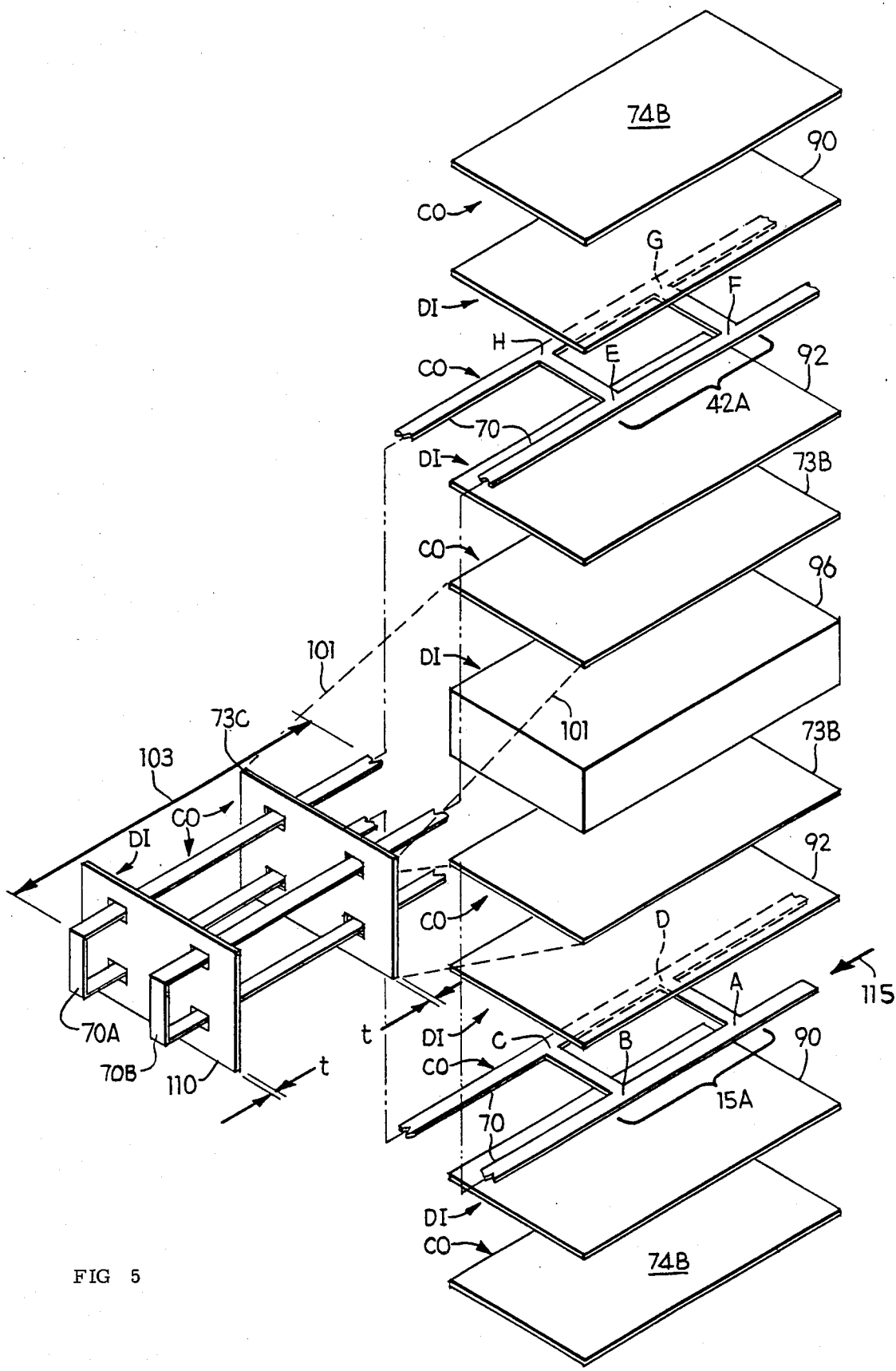
FIG. 5 illustrates the construction of a sensor in which the hybrid circuits 15 and 42 of FIG. 1 are integrated into the construction of the sensor of FIG. 2.

A detailed diagram of another form of the sensor 25 is shown in FIG. 5. The sensor 25 in FIG. 5 is similar to that in FIG. 3, but an added feature is that the function of signal splitters 15 and 42 in FIGS. 1 and 6 is assumed by regions 15A and 42A of striplines 70. The configuration sketched in the Figure is generally referred to as a branched-line coupler. Dielectric regions 90, 92, and 110 are shown in this exploded diagram. The length 103 in FIG. 5 is shown greatly exaggerated. In practice, 70A is separated from 73C by a distance comparable to that between 70 and 73B.

A significant advantage of the sensor shown in FIG. 5 is the integration of the sensing lines and signal splitters 15 and 42 into one module. In contrast, the splitters are external to the sensor 25 in FIG. 1. Thus, if the input signal is represented by arrow 115 in FIG. 5, the signals reaching points B and C will be equal and 90 degrees out of phase. If no change occurs in 70A, then 42A will recombine the signals such that they are in phase and add at G, and a null signal will be seen at F. If the sensor is designed and manufactured to precise tolerances, the need for the external phase shifter 39 in FIGS. 1 and 6 is eliminated, or its function may be assumed by trimming (i.e., modifying the geometry) adjustments. Further, the natural symmetry of construction will avoid many environmental effects on performance.

The Inventor points out that it is not generally the actual phase difference which is measured or even sought. It is the difference in the voltage at point F in the presence of an object, as compared with the voltage at the same point in the absence of the object which is generally useful as an end result of the foregoing argument. As FIG. 7 shows, this voltage is a function of the distance 64 in FIG. 1 between the object 30 and sensor 25. Further, this voltage is approximately a logarithmic function of the distance for sensors and objects tested.

Figure 8:
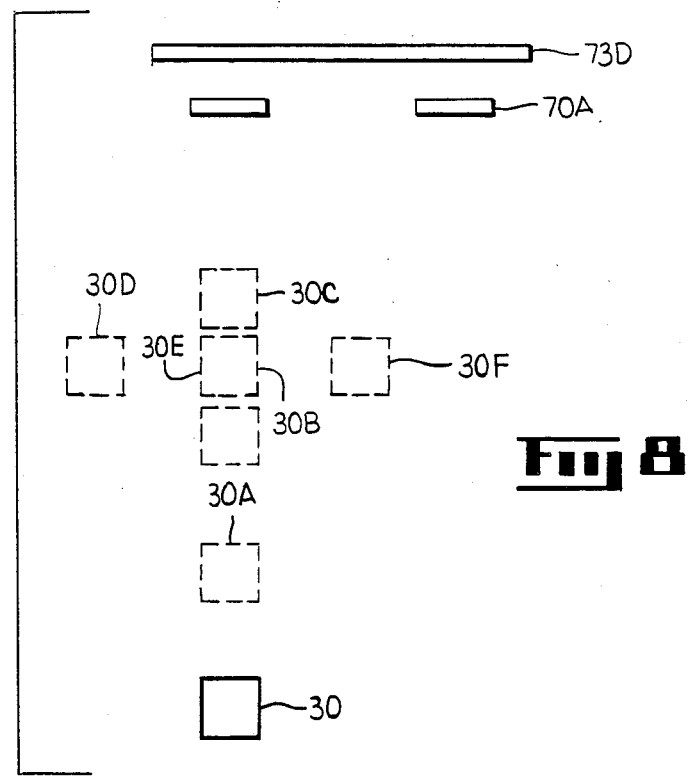
FIG. 8 indicates the geometrical motions for calibration curves.

The term distance has been used loosely in the discussion above. FIG. 8 illustrates a cross section of the sensor of FIG. 2, taken along lines 8—8. If an object 30 is moved to successive positions indicated by phantom blocks 30A-C, a voltage-distance plot resembling that of FIG. 7 will be obtained. However, if the object is moved along a different path, such as that shown by phantom objects 30D-F, a different plot such as that of FIG. 9 may be obtained, for various distances of closest approach. The sensor is calibrated as described above for a given object shapes and known path.

Figure 10:
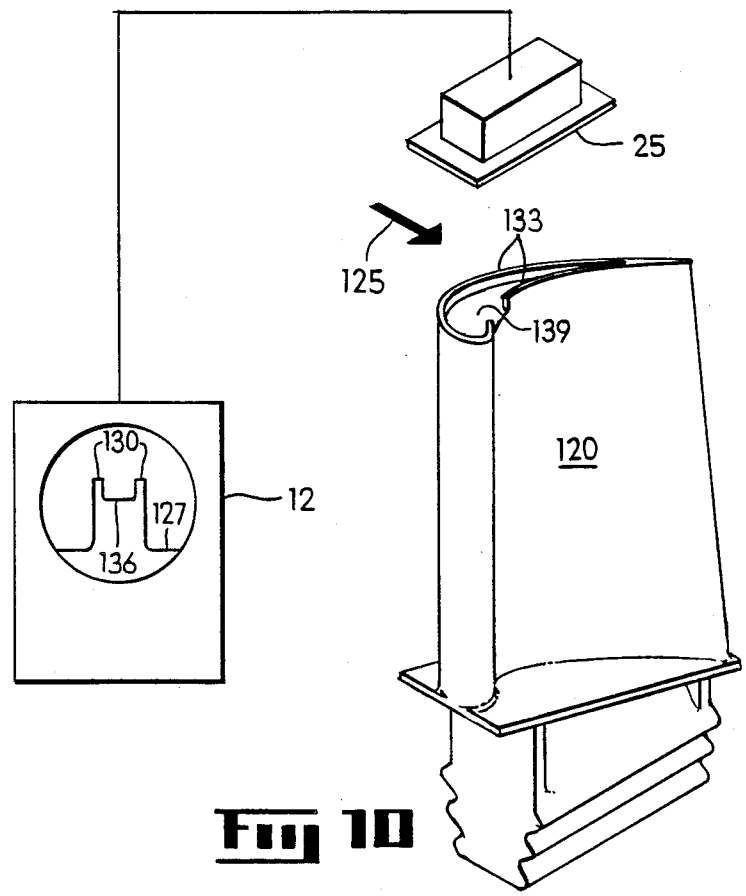
FIG. 10 indicates the performance when a typical complex object is measured.

The relative geometry is easily inferred for many measurements. For example, if a gas turbine engine blade 120 in FIG. 10 traverses the region near the sensor 25 as shown by the arrow 125. A signal 127 on the oscilloscope 12 is obtained which resembles that shown. The oscilloscope signal gives a signature of the geometry of the blade. For example, peaks 130 correspond to what are called in the art as squealer tips 133 on the blade 120, and valley 136 would correspond to region 139 on the blade 120. Thus, in the gas turbine art, the invention can be used to measure the clearance between turbine blades and a turbine shroud, or to obtain the signature of the blade tip. In the latter case, a deviation in signature by another blade can indicate a deviation in blade geometry, which is useful in testing. The deviation can indicate damage in the blade. In the former case, clearance (i.e., a distance similar to distance 64 in FIG. 1) measurement can be useful in the control of turbine clearance in gas turbine engines. For example, in U.S. Pat. No. 4,230,436, issued to Samuel H. Davison, on Oct. 28, 1980, and assigned to General Electric Company, which is hereby incorporated by reference, a system for controlling the turbine clearance is described. The present invention can provide real-time immediate information as to actual turbine clearance, as an input to the control system.

An invention has been described wherein an object present near one of two transmission lines changes the speed of propagation in the line, thus altering the phase of the signals in the lines. Measurement of the phase change, as by phasor addition of the signals when the object is absent, and again when the object is at known positions, and comparing the two added signals allows one to establish a calibration curve as in FIG. 7. Later measurements of the signals in the presence of the object at an unknown distance, such as that at point 185 in FIG. 7, indicates that the distance to the object is distance 189.

As discussed in connection with FIG. 7 and 8, it is recognized that use of FIG. 7 only applies to a situation similar to the one under which FIG. 7 was generated. A collection of such points, however, as the object moves in a known manner, may be used to infer additional information.

Numerous substitutions and modifications can be undertaken without departing from the true spirit and scope of the present invention.

For example, the term splitter has been used to describe elements 15 and 42. However, any microwave power divider, hybrid, or 3 dB directional coupler can be used to accomplish an equivalent result, namely, providing signals of identical frequency with known magnitude and phase at points 18 and 21, as well as combining the signals on lines 33 and 36 in a known manner in order to measure the phase shift occurring along sensors 27 and 28.

Also, a diode 51 was described in FIG. 1. However, other forms of microwave demodulators or receivers can be used to accomplish the rectification. In particular, a microwave mixer and superheterodyne receiver with logarithmic amplifiers can be used to accomplish an improved result. The latter combination provides a linear output which increases the dynamic range of the device.

What is desired to be secured by Letters Patent of the United States is the invention as defined in the following claims.

1. A sensor for use in a system for measuring distance, comprising:
   (a) a transmission line including at least two conductive strips, each of which carries a signal, with at least one ground plane near the strips; and
   (b) a discontinuity in the ground phane for allowing the phase of the signal in at least one of the strips to be altered by a change in a dielectric medium nearby the transmission line.

2. Apparatus according to claim 1 and further comprising:
   sensing means for sensing the change in phase for indicating distance to the object.

3. A sensor for use in a system which provides a signal indicative of distance between the sensor and an object comprising:
   (a) first and second conductors (70A) for carrying respective first and second signals having a relative propagation velocity which can be changed by the presence of a nearby object;
   (b) first splitter means (15) for applying first and second input signals to the first and second conductors, respectively, with a predetermined, non-zero, phase difference between the signals; and
   (c) second splitter means (42) for receiving the first and second input signals from the first and second conductors and for combining the first and second signals into an output signals containing information as to distance to the nearby object.

* * * * *